(12) United States Patent
Conca et al.

(10) Patent No.: US 7,572,752 B2
(45) Date of Patent: *Aug. 11, 2009

(54) METHOD FOR PREPARING A CATALYST FOR OXIDATION OF METHANOL TO FORMALDEHYDE

(75) Inventors: Esterino Conca, Novara (IT); Carlo Rubini, San Fermo Della Battaglia (IT); Marcello Marchi, Novara (IT)

(73) Assignee: Sud-Chemie Catalysts Italia S.R.L., Novara (IT)

( * ) Notice: Subject to any disclaimer, the term of this patent is extended or adjusted under 35 U.S.C. 154(b) by 0 days.

This patent is subject to a terminal disclaimer.

(21) Appl. No.: 11/303,500

(22) Filed: Dec. 16, 2005

(65) Prior Publication Data

US 2006/0142619 A1    Jun. 29, 2006

(30) Foreign Application Priority Data

Dec. 23, 2004   (IT)   ................ MI2004A2500

(51) Int. Cl.
  *B01J 23/00*  (2006.01)
  *B01J 23/40*  (2006.01)
  *B01J 23/42*  (2006.01)
  *B01J 23/70*  (2006.01)
  *B01J 23/74*  (2006.01)

(52) U.S. Cl. ............... 502/313; 502/304; 502/326; 502/336; 502/338

(58) Field of Classification Search ............... 502/304, 502/313, 326, 336, 338
See application file for complete search history.

(56) References Cited

U.S. PATENT DOCUMENTS

| | | | | |
|---|---|---|---|---|
| 2,812,310 A | | 11/1957 | Walker et al. | |
| 3,198,753 A | * | 8/1965 | Traina | 502/316 |
| 3,716,497 A | * | 2/1973 | Courty | 502/302 |
| 3,821,151 A | * | 6/1974 | Mitchell | 524/406 |
| 3,975,302 A | * | 8/1976 | Courty et al. | 502/263 |
| 3,978,136 A | * | 8/1976 | Friedrich et al. | 568/474 |
| 3,983,073 A | * | 9/1976 | Trifiro et al. | 502/316 |
| 4,000,085 A | * | 12/1976 | Courty et al. | 252/634 |
| 4,024,074 A | * | 5/1977 | Cairati et al. | 502/311 |
| 4,141,861 A | * | 2/1979 | Courty et al. | 502/302 |
| 4,181,629 A | * | 1/1980 | Cairati et al. | 502/255 |
| 4,317,675 A | * | 3/1982 | Nishihara et al. | 75/348 |
| 4,323,395 A | * | 4/1982 | Li | 419/35 |
| 4,829,042 A | * | 5/1989 | Cavalli et al. | 502/316 |
| 4,954,171 A | * | 9/1990 | Takajo et al. | 75/246 |
| 5,580,839 A | * | 12/1996 | Huffman et al. | 502/338 |
| 5,599,377 A | * | 2/1997 | Uenosono et al. | 75/252 |
| 6,068,813 A | * | 5/2000 | Semel | 419/66 |
| 6,331,503 B1 | * | 12/2001 | Wachs et al. | 502/305 |
| 6,624,332 B2 | * | 9/2003 | Wachs et al. | 568/470 |
| 6,756,083 B2 | * | 6/2004 | Holmqvist et al. | 427/456 |
| 6,930,072 B2 | * | 8/2005 | Wachs et al. | 502/307 |
| 2002/0062048 A1 | * | 5/2002 | Wachs et al. | 568/487 |
| 2002/0087031 A1 | * | 7/2002 | Wachs et al. | 568/474 |
| 2002/0197500 A1 | * | 12/2002 | Holmqvist et al. | 428/570 |
| 2004/0206204 A1 | * | 10/2004 | Holmqvist et al. | 75/255 |
| 2006/0135821 A1 | * | 6/2006 | Conca et al. | 568/474 |

FOREIGN PATENT DOCUMENTS

| | | |
|---|---|---|
| EP | 0 199 359 A2 * | 10/1986 |
| GB | 1 191 143 A | 5/1970 |
| GB | 1 282 950 A | 7/1972 |
| WO | WO 03/053556 A | 7/2003 |

OTHER PUBLICATIONS

Li Jin-Lu, Zhang Yu-Xiang, Liu Chong-Wei, Zhu Qi-Ming: "Improvement in reactivity, reproducibility and stability of Fe-Mo catalysts by wet mixing" Catalysis Today, vol. 51 . . . .

Roy A et al: "Mossbauer studies on Zn-substituted iron molybdate" Material Research Bulletin, Elsevier, Kidlington, GB, vol. 37, No. 14, Nov. 20, 2002 . . . .

* cited by examiner

*Primary Examiner*—Cam N. Nguyen
(74) *Attorney, Agent, or Firm*—Husch Blackwell Sanders LLP Welsh & Katz

(57) ABSTRACT

Process for preparing a catalyst for the oxidation of methanol to formaldehyde, comprising reacting iron powder and molybdenum trioxide in a Mo/Fe ratio from 1.5 to 5 in an aqueous suspension at temperatures from 20 to 100° C., and subsequently, optionally simultaneously, oxidizing the mixture with an oxidizing agent in a quantity equal to, or greater than the quantity required for the oxidation of the ferrous ion to ferric ion and to oxidize the molybdenum to the valence state 6.

8 Claims, No Drawings

METHOD FOR PREPARING A CATALYST FOR OXIDATION OF METHANOL TO FORMALDEHYDE

BACKGROUND OF THE INVENTION

The present invention relates to a method for preparing a catalyst for oxidation of methanol to formaldehyde and to its use in processes for preparing formaldehyde.

Catalysts for the oxidation of methanol to formaldehyde (commonly termed "iron molybdate", since $Fe_2(MoO_4)_3$ is one of the main active components) comprise a $Fe_2(MoO_4)_3/MoO_3$ mixture in which the Mo/Fe ratio is comprised between 1.5 and 5, and are generally prepared according to a method which comprises the precipitation of the above catalytic mixture from an aqueous solution of a soluble ferric salt, such as $FeCl_3$, $Fe(NO_3)_3$ and the like, mixed with a solution of an alkaline molybdate or of ammonium, subsequent dilution of the suspension, filtration and washing of the precipitate, its conversion into a slurry by agitation, drying of the slurry and subsequent shaping of the dried powder or of a paste thereof so as to obtain granules having a specific geometric shape, and calcination of the granules at temperatures generally from 450 to 550° C.

Precipitation is performed from solutions with relatively low pH values (comprised from 1 to 2 in the case of precipitation from ferric chloride solutions), at which there is a significant solubilization of iron molybdate.

The discharge of the mother liquors and wash water containing molybdate ions as well as ammonium, ferric, nitrate and chloride ions becomes problematic, because these ions are pollutants and statutory provisions currently in force in many countries prohibit their discharge or allow it at concentrations far lower than those of the mother liquors and/or wash water.

SUMMARY OF THE INVENTION

A method has now been found unexpectedly for preparing a catalyst comprising $Fe_2(MoO_4)_3/MoO_3$ mixtures in which the Mo/Fe ratio is comprised from 1.5 to 5 and allows to avoid the discharge of mother liquors and/or wash water and thus does not have the problems of the prior art processes.

Another advantage of the method according to the invention resides in that it allows to obtain catalysts that do not contain anions of ferric salts such as chloride ions, which are always present, albeit in small amounts, in the catalysts prepared according to the methods of the prior art. In the catalysts prepared according to the new process, there are practically no impurities deriving from ions of alkali metals, and if there are any, their quantity is lower than 40 ppm.

DESCRIPTION OF THE PREFERRED EMBODIMENTS

The method according to the present invention comprises the reaction of iron in powder form suspended in water with molybdenum trioxide, followed by an oxidizing treatment with hydrogen peroxide or other oxidizing agent in a quantity equal to, or greater than, the quantity required to oxidize the ferrous ion to ferric ion and to oxidate molybdenum to the hexavalent state. As an alternative, the oxidizing agent can be dosed during the reaction between iron and molybdenum oxide.

The Mo/Fe atomic ratio in the reaction is comprised from 1.5 to 5, preferably 2.5-3; the process is performed at temperatures comprised from about 20° C. and the boiling point of the mass (100° C.), preferably 60-80° C. Once the reaction has been completed, the suspension of the precipitate is diluted and the mother liquors are separated and recycled; the precipitate is dried and the powder or a paste thereof is subjected to shaping to obtain granules having a specific geometric shape, particularly cylindrical granules provided with a through bore or granules having a three-lobed cross-section provided, at the lobes, with through bores parallel to the axis of the granule.

The granules are activated by calcination at temperatures from 450 to 600° C., preferably from 480 to 580° C.

The iron in powder form is preferably used in the form of microspheroidal particles with an average diameter of 40 to 150 microns.

The carbon content in the iron is generally lower than 0.15% by weight. Elements such as for example nickel, copper, silicon and manganese can be present in quantities preferably lower than 1%. Manganese is generally always present and can thus constitute a marker of the new process. The hydrogen peroxide or equivalent oxidizers such as oxygen, organic peroxides or hydroperoxides are preferably used in excess with respect to the quantity needed for oxidation of the ferrous ion to ferric ion and to oxidate molybdenum to the hexavalent state.

The resulting catalyst, thanks to the absence of impurities derived from the reagents used in the preparation processes of the prior art, has a constant performance for significantly long periods of time.

The performance of the catalyst can be improved further by adding cerium molybdate, with the cerium tri- or tetravalent, in a quantity from 0.05 to 10% by weight as cerium, preferably 0.1-5%. Cerium molybdate in fact has the effect of lowering significantly the hot-spot temperature in the catalytic bed, thus increasing the stability of the catalytic bed and therefore its life.

The addition of cerium molybdate is performed by mixing, after decantation of the mother liquors, a precipitate obtained according to the method of the present invention and a precipitate of cerium molybdate obtained from a solution of a trivalent and/or tetravalent soluble cerium salt, such as for example cerium carbonate, mixed with a solution of a molybdate of alkali metals and/or ammonium (followed by washing in order to eliminate the extraneous ions); or from cerium carbonate and molybdenum trioxide in aqueous suspension, heated until the generation of $CO_2$ ceases; or with a method similar to the preceding one, by adding molybdenum trioxide and cerium carbonate directly to the mixture during the reaction between iron and molybdenum oxide.

The X-ray diffraction (XRD) spectrum recorded in high-resolution conditions of a catalyst containing cerium molybdate shows lines which, at a relatively low cerium concentration (3000 ppm), appear at lattice distances d=8.44 Å; d=6.69 Å and d=4.79 Å, while for higher concentrations (17000 ppm) there are lines which appear at distances d=8.53 Å; d=6.74 Å; d=4.82 Å and lines at distances d=4.29 Å; d=3.37 Å and d=2.75 Å.

High-resolution XRD analysis is performed by using a Panalytical X'Pert theta/2 theta automated powder diffractometer with Bragg-Brentano geometry, using Cu $K_a$ X radiation with lambda=1.54184 Å and 1.6 kW of power. The angular interval used is 5° to 125° 2 theta with steps of 0.01° and an acquisition time of 15 seconds per step. The extended description of the goniometer provides two 0.04-rad Soller slits, 1° divergence and antiscatter slits, and an 0.4-mm receiving slit. The diffracted beam is further collected by a secondary graphite monochromator.

Both the catalyst containing cerium molybdate and the molybdate-free catalyst have a surface area of 1 to 7 m²/g, preferably 2-6 m²/g.

Methanol oxidation is performed according to known methods.

The gas mixtures contain methanol in a concentration from 6 to 10% by volume and oxygen in a concentration from 9 to 13% by volume, the remainder being inert gas such as for example nitrogen. The reactor is of the bundle-tube type and the reaction heat is removed by a coolant liquid which circulates outside the pipes.

The linear velocity of the gases is 1-2 Nm/sec; the temperature of the bath is comprised from 250 to 320° C.

Preferably, the gas mixture is fed into the reactor at temperatures from 120 to 160° C.

The following examples are given to illustrate but not to limit the present invention.

EXAMPLES

The pilot plant for the catalytic tests of the oxidation of methanol to formaldehyde is constituted by a tubular reactor immersed in a molten-salt bath. The reactor is 1950 mm long and has an inside diameter of 20.4 mm. The catalyst is located in the central part of the reactor so as to ensure maximum isothermicity. The molten-salt bath is heated by means of electric immersion heaters and the temperature is controlled by a regulator.

The gases are introduced from the upper region of the reactor.

The air and nitrogen are dosed by mass-flow and the methanol is dosed by means of a constant-flow pump and sent first to an evaporator.

The flow at the exit from the reactor and the gases after the purge column are analyzed by gas chromatography.

Example 1

11 liters of water are loaded into a reactor having a volume of 20 liters, provided with an agitator and with a temperature control system. The liquid is agitated and then 128 g of metallic iron in powder form and 825 g of $MoO_3$ are loaded into said reactor. The mass is heated to 75° C. and is left in these conditions for 20 hours. At the end a dark blue suspension is formed. The suspension is cooled to 65° C. and treated with 35% hydrogen peroxide (approximately 1.4 liters) by means of a peristaltic pump and until it assumes a yellow color. Oxidation lasts approximately 3 hours.

The precipitate is filtered, dried, pelletized (after lubrication) in the form of a perforated cylinder, and activated in air at 500° C. for 4 hours.

Example 2

The preparation of Example 1 is repeated, adding to the reagent mass 7.1 g of cerium carbonate (42% Ce) and 4.6 g of $MoO_3$; the test conditions are the same as in Example 1.

Example 3

Conditions of the Catalytic Tests

The catalytic bed is constituted by two layers: an upper layer of 400 mm of ceramic rings, and a lower layer of 700 mm of catalyst.

The total flow-rate of the inlet gases is 1.5 Nm/sec (1765 Nl/hour).

The $O_2$ content of the mixture at inlet is approximately 9.5%.

Table 1 reports the results obtained by using the catalyst of Example 1 Table 2 reports the results obtained by using the catalyst of Example 2.

TABLE 1

| Bath temperature ° C. | Methanol at inlet % | Methanol conversion % | Formaldehyde yield % |
|---|---|---|---|
| 250 | 6.03 | 94.74 | 87.79 |
| 255 | 6.01 | 96.75 | 89.92 |
| 260 | 6.03 | 98.06 | 91.43 |
| 265 | 6.03 | 98.67 | 91.85 |

TABLE 2

| Bath temperature ° C. | Methanol at inlet % | Methanol conversion % | Formaldehyde yield % |
|---|---|---|---|
| 250 | 6.02 | 94.35 | 87.69 |
| 255 | 6.03 | 96.49 | 90.10 |
| 260 | 6.01 | 97.73 | 91.34 |
| 265 | 6.04 | 98.62 | 92.12 |

The disclosures in Italian Patent Application No. MI2004A002500 from which this application claims priority are incorporated herein by reference.

What is claimed is:

1. A process for preparing a catalyst for the oxidation of methanol to formaldehyde, comprising forming a mixture by reacting iron powder and molybdenum trioxide in a Mo/Fe atomic ratio from 1.5 to 5 in an aqueous suspension at a temperature range of 20 to 100° C., and, then oxidizing the mixture with hydrogen peroxide in a quantity equal to, or greater than the quantity required for the oxidation of the ferrous ion to ferric ion and to oxidize the molybdenum to the valence state 6, thereby forming a precipitate.

2. The process according to claim 1, wherein the reaction of the iron powder and molybdenum trioxide is performed at a temperature range of 60 to 80° C.

3. The process according to claim 1, wherein the mother liquors of the reaction are separated and recycled, the precipitate is dried to form a powder or paste and the powder or a paste is subjected to shaping to obtain granules having a specific geometric shape, and the granules are calcined at a temperature range of 450 to 600° C.

4. The process according to claim 3, wherein the granules are calcined at a temperature range of 480 to 580° C.

5. The process of claim 1 wherein the step of oxidizing is carried out subsequent to the step of reacting iron powder and molybdenum trioxide.

6. The process of claim 1 wherein the step of oxidizing is carried out simultaneous with the step of reacting iron powder and molybdenum trioxide.

7. A catalyst for oxidizing methanol to formaldehyde, comprising a catalytic mixture $Fe_2(MoO_4)_3$/ $MoO_3$ wherein the Mo/Fe atomic ratio is from 1.5 to 5, the catalyst is free from anions of iron salts and from alkali metals ions and/or ammonium ion.

8. The catalyst according to claim 7, comprising cerium molybdate in quantities from 0.05 to 10% by weight as cerium.

* * * * *